United States Patent
Matsutani et al.

(10) Patent No.: US 7,356,898 B2
(45) Date of Patent: Apr. 15, 2008

(54) SURGICAL KNIFE PRODUCTION METHOD

(75) Inventors: Kanji Matsutani, Takanezawa-machi (JP); Takashi Ina, Takanezawa-machi (JP); Masahiko Saitoh, Takanezawa-machi (JP); Mitsuru Saitoh, Takanezawa-machi (JP)

(73) Assignee: MANI, Inc., Tochigi (JP)

( * ) Notice: Subject to any disclaimer, the term of this patent is extended or adjusted under 35 U.S.C. 154(b) by 596 days.

(21) Appl. No.: 10/439,921

(22) Filed: May 16, 2003

(65) Prior Publication Data
US 2004/0089159 A1    May 13, 2004

Related U.S. Application Data

(63) Continuation-in-part of application No. 09/643,351, filed on Aug. 23, 2000, now abandoned.

(51) Int. Cl.
*B21C 37/30* (2006.01)
*A61F 9/00* (2006.01)

(52) U.S. Cl. .................. 29/90.7; 29/557; 606/166; 606/172; 30/353

(58) Field of Classification Search .......... 29/90.7, 29/557; 606/166, 167, 172; 30/346, 353, 30/357
See application file for complete search history.

(56) References Cited

U.S. PATENT DOCUMENTS

| | | | | |
|---|---|---|---|---|
| 4,126,136 A * | 11/1978 | Auth et al. | ..................... | 606/3 |
| 4,674,498 A * | 6/1987 | Stasz | ........................... | 606/48 |
| 5,222,965 A * | 6/1993 | Haughton | .................... | 606/159 |
| 5,352,233 A * | 10/1994 | Anis | ........................... | 606/167 |
| 5,718,708 A * | 2/1998 | Webb | ........................... | 606/107 |
| 2002/0083598 A1* | 7/2002 | Julien | .......................... | 30/350 |

FOREIGN PATENT DOCUMENTS

WO      WO97/29892      * 8/1997

* cited by examiner

*Primary Examiner*—David P. Bryant
*Assistant Examiner*—Sarang Afzali
(74) *Attorney, Agent, or Firm*—Muramatsu & Associates

(57) ABSTRACT

A method for producing a surgical knife of a very small size for use in ophthalmic surgery under a microscopic environment having a sharp edge without causing reflection of lights. The surgical knife comprises a handle, and a blade attached to the handle. The blade has a sharp polished cutting edge, a rough machined surface provided inside of the cutting edge having a relatively rough surface area, and an inner flat area. An anti-reflection treatment is provided on an upper and lower surfaces of the blade except for the cutting edge, thereby prohibiting reflection or emission of lights from the knife.

2 Claims, 3 Drawing Sheets

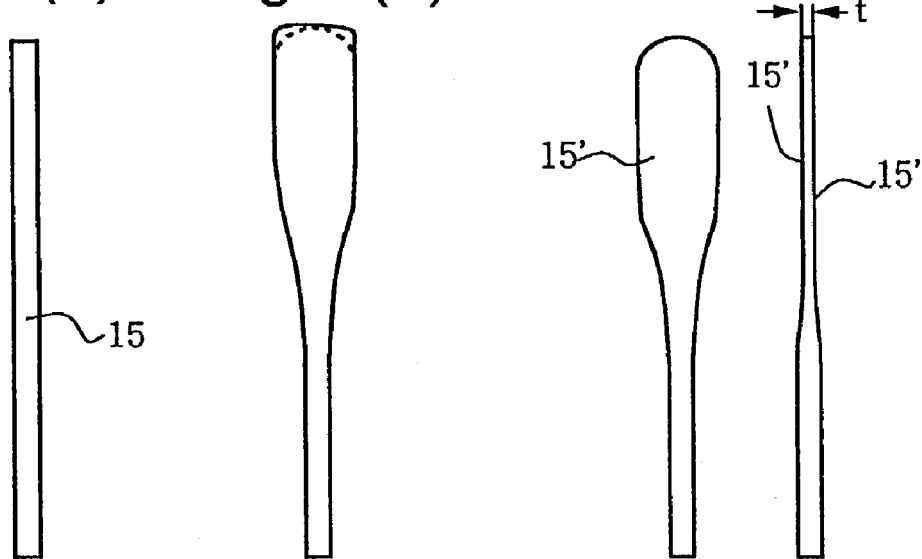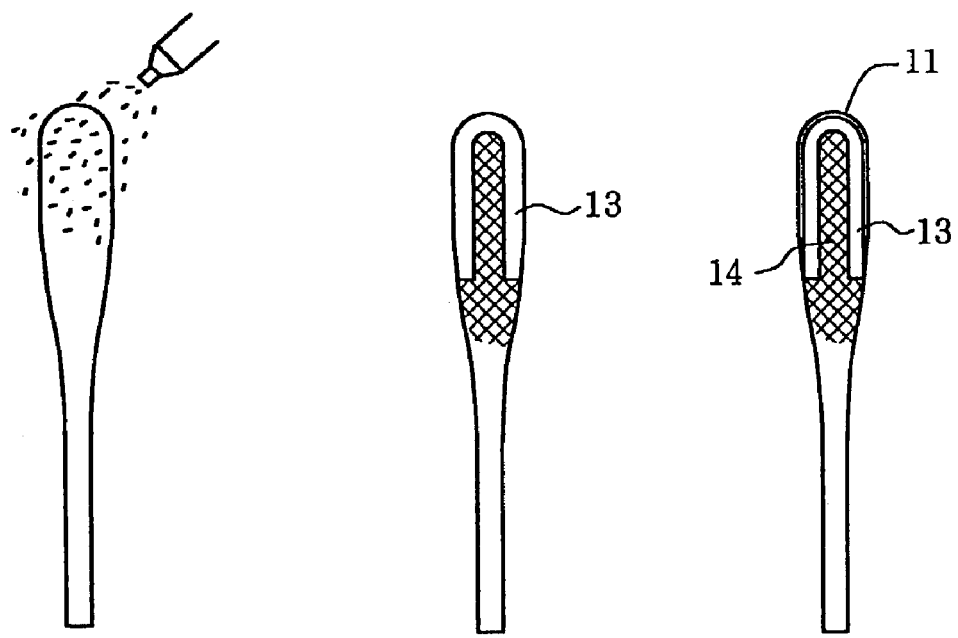

SURGICAL KNIFE PRODUCTION METHOD

This is a continuation-in-part of U.S. application Ser. No. 09/643,351 filed Aug. 23, 2000, now abandoned.

FIELD OF THE INVENTION

This invention relates to a method of producing a surgical knife or scalpel for performing a surgical operation, and more particularly, to a method of producing a surgical knife of a very small size used in ophthalmic surgery under a microscopic environment having a sharp edge without causing reflection of lights.

BACKGROUND OF THE INVENTION

In performing a surgical operation, especially an ophthalmic surgery such as a cataract operation, which involves cutting cornea or sclera through microscopic observation, an ophthalmic surgery knife or scalpel is used. Such a surgical knife is very small having, for example, a thickness of 0.10-0.30 mm and a width of 1.5-3.5 mm. Incisions made by the surgical knife will be closed either through a suture or through a natural adhesion without suture.

To achieve a natural adhesion of the incisions, such incisions must be made by an extremely sharp blade of the surgical knife. To have very sharp blades, cutting edges of the surgical knife must be sufficiently polished, thereby having mirror polished surfaces.

In an ophthalmic surgery, a surgeon uses a microscope to observe a magnified object to perform a very delicate surgery in an extremely small area to make an incision accurately.

Since such a microscope involves a lighting to sufficiently produce the magnified image of the object, the mirror polished edges of the surgical knife tends to cause a reflection of the lights or glare. Such a reflection or glare adversely affects the visibility of the object for the surgeon, making the surgical operation difficult.

Thus, a surgical knife having an anti-reflection treatment on a part thereof in a visual field through the microscope has been proposed. Such an anti-reflection treatment is made through a chemical process to form a large number of crater like bumps on the surface of the surgical knife or through a barrel buffing or sandblasting process to form irregularities on the surface of the knife. Because of the bumps or irregularities on the surgical knife, the light is reflected irregularly and randomly, thereby avoiding the glare or reflection in the surgical operation.

Although the surgical knife having the anti-reflection treatment is effective in eliminating the reflection by the surgical knife, the sharpness of the blade tends to be harmed because such irregularities of the surface extend to the cutting edges of the knife.

The sharpness of the surgical knife is very important in the ophthalmic surgery, since the above noted natural adhesion is largely dependent upon the smoothness of the inner surface of the incision. If the inner surface of the incision is rough, it may cause a distortion after suturing the incision or may cause astigmatism. Therefore, a successful surgical operation is dependent upon whether the surgical knife has sufficient sharpness. Especially, a high level of sharpness in the surgical knife is required in an ophthalmic surgical operation that involves cornea cutting since it requires a surgeon to make complicated incisions. However, the conventional method for producing a surgical knife is insufficient to achieve such a high level of sharpness while prohibiting reflection or emission of lights from the knife.

SUMMARY OF THE INVENTION

This invention has been made to solve the problems involved in the surgical knife produced through the conventional technology.

It is, therefore, an object of the present invention to provide a method for producing a surgical knife which has a high level of sharpness in the cutting edge and is capable of preventing reflection of light.

It is another object of the present invention to provide a method of producing a surgical knife which is capable of accurately and correctly performing the surgical operation by having a scale showing a depth of cut and other information such as a type of knife on the surface thereof.

It is a further object of the present invention to provide a method of producing a surgical knife which has a high level of sharpness in the cutting edge and an anti-reflection treatment.

In the present invention, a surgical knife of high level of sharpness with anti-reflection treatment is produced, which is used in a surgical operation using a microscope. The surgical knife is provided with an anti-reflection treatment in a visual field of the microscope, and is characterized in that the surgical knife has a portion which has no anti-reflection treatment. The portion having no anti-reflection treatment includes at least an edge of the knife. The surgical knife further includes scale and/or characters on the area having the anti-reflection treatment.

The surgical knife of the present invention includes a handle, and a blade attached to the handle. The blade has a sharp polished cutting edge, a rough machined surface provided inside of the cutting edge having a relatively rough surface area, and an inner flat area. An anti-reflection treatment is provided on an upper and lower surfaces of the blade except for the cutting edge, thereby prohibiting reflection or emission of lights from the surgical knife. The surgical knife has a very small size wherein width of the cutting edge is about 0.15 mm, and width of the rough machining surface is about 0.35 mm.

The anti-reflection treatment is performed through a sandblasting process or a barrel buffing process. In other methods, the anti-reflection treatment is performed through an oxide coating process or a painting process.

According to the present invention, since the surgical knife has the anti-reflection treatment on the overall area except for the cutting edge, it can maintain the sharpness of the cutting edge while being able to prevent the glare from the knife during the surgical operation. Thus, the surgeon can perform the surgical operation accurately without being affected by the glare.

BRIEF DESCRIPTION OF THE DRAWINGS

FIG. 1 shows a crescent knife in the present invention where

FIGS. 3(a)-3(g) are schematic diagrams showing an example of process for producing a surgical knife of the present invention.

DETAILED DESCRIPTION OF THE INVENTION

The surgical knife of the present invention will be described in detail with reference to the accompanying drawings wherein like numerals refer to like parts throughout. FIGS. 1(a)-1(d) show a first embodiment of a surgical knife 10 which is called a crescent knife. As noted above, an actual size of the knife is very small, thus, FIGS. 1(a)-1(d) show enlarged views of the surgical knife of the present invention.

Figure 1A:
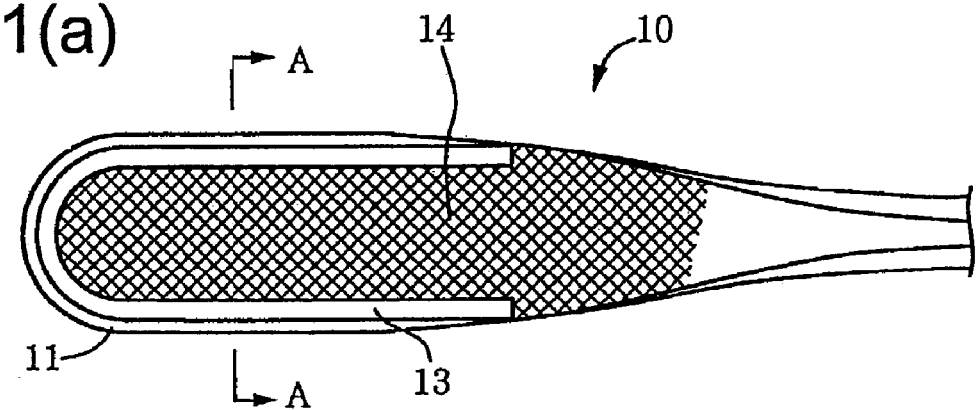
FIG. 1(a) is a top view thereof.
Figure 1B:
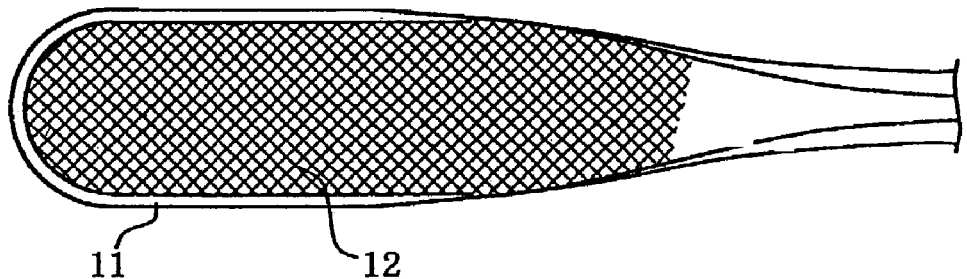
FIG. 1(b) is a bottom view thereof.
Figure 1C:
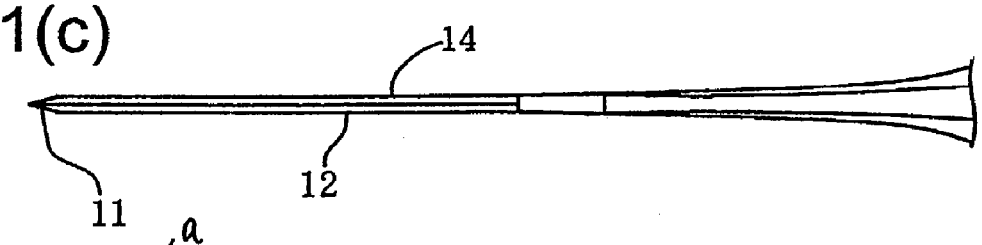
FIG. 1(c) is a side view thereof.
Figure 1D:
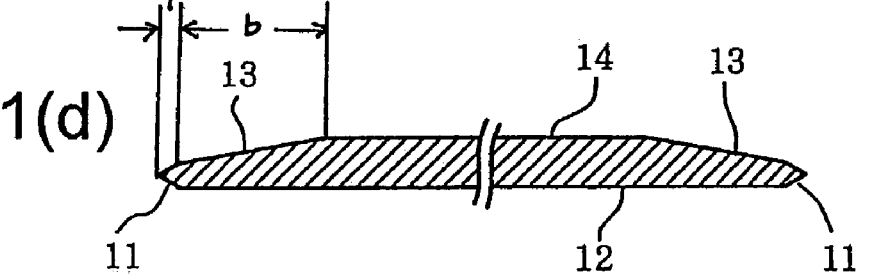
FIG. 1(d) is an enlarged cross sectional view taken along the A-A line of FIG. 1(a).

More particularly, FIG. 1(a) is a top view of the surgical knife of the present invention, FIG. 1(b) is a bottom view thereof, FIG. 1(c) is a side view thereof, and FIG. 1(d) is a cross sectional view taken along the A-A line of FIG. 1(a). As shown in the drawings, the surgical knife 10 is made by flattening an end of a rod and the like. The rod itself may be a handle of the surgical knife or connected to the handle of the surgical knife. Thus, the tip (blade) of the knife 10 has a shape of semicircular plate with a U-shaped side edge 11 at its circumference. A bottom surface 12 of the knife 10 is flat which is provided with an anti-reflection treatment as a whole except for the side edge 11. On an upper surface of the knife 10, there is provided with a rough machined surface 13 with a U-shape in top view along the side edge 11 and with a gentle inclination. On the upper surface, an area inside of the U-shaped rough machined surface 13 including a flat center area 14 also has an anti-reflection treatment.

Such an anti-reflection treatment is made through a chemical process or an electrical process to form a large number of crater like bumps on the surface of the surgical knife or through a mechanical process including a barrel buffing or sandblasting process to form irregularities on the surface of the knife. Other methods include an oxide coating process such as molten salt or electrolysis to form a color coating (dark color) on the knife and a painting process to paint the surface of the knife.

When the surgical knife 10 of the present invention is used under the microscope observation to perform an ophthalmic surgery such as cutting cornea, the surgeon is not interrupted by the glare since the surgical knife 10 has the anti-reflection treatment on the flat center area 14. The side edge 11 has been sufficiently polished, thus, the surgical knife 10 maintains a high level of sharpness.

In this surgical knife, the rough machined surface 13 and the side edge 11 are not provided with the anti-reflection treatment. Since the rough machined surface 13 has a rougher surface relative to a polished surface, a degree of reflection of light is low. Further, since the rough machined surface 13 and the side edge 11 are inclined, and thus, the directions of reflection are different from the other part, which do not cause a large degree of glare.

In the present invention, it is also possible to make use of the difference of reflection between the rough machined surface 13 and the inner center area 14 for determining a depth of cut in inserting the knife into the incision. For example, with reference to FIG. 1(d), width a of cutting edge 11 of the crescent knife is about 0.15 mm, and width b of the rough machining surface 13 is about 0.35 mm. Thus, for example, when inserting the knife until the border line of the cutting edge 11 and the rough machined surface 13, the depth of cut in the incision can be judged as 0.15 mm.

Figure 2:
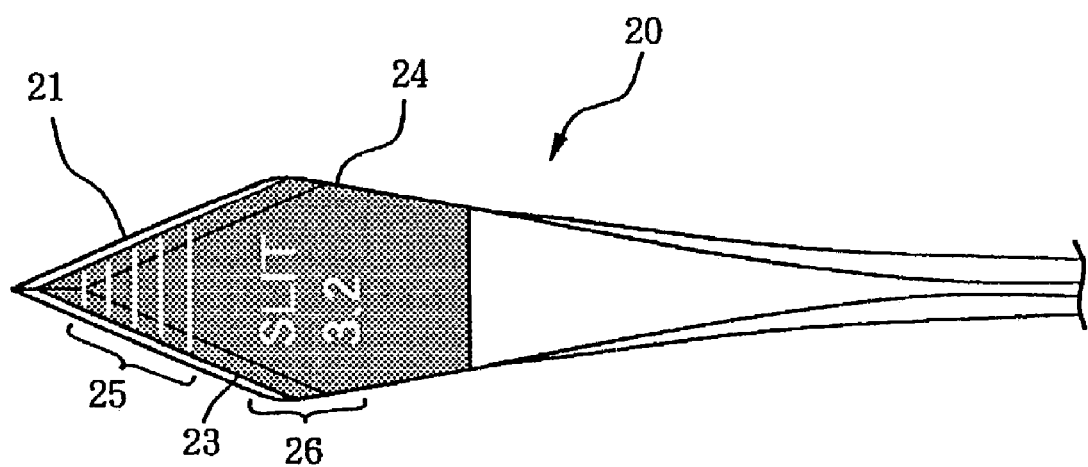
FIG. 2 is a top view showing a slit knife in accordance with the present invention.

FIG. 2 shows a second embodiment of the present invention which is a top view of a slit knife 20. In this example, a cutting edge (blade) 21 has a V-shape at the left side of FIG. 2. Similar to the example of crescent knife, an inner area of the knife along the cutting edge 21 has a rough machined surface 23 which is gently inclined. A further inner area of the knife 20 is a flat surface 24. On the upper and lower surfaces of the knife 20, except for the cutting edge 21, the anti-reflection treatment is provided on the whole surfaces including the rough machined surface 23.

In the example of FIG. 2, the surgical knife 20 includes a scale 25 on the left end and characters 26 at around a middle portion thereof. The scale 25 includes several vertical lines to show the distance from the tip of the knife. In this example, the scale has five lines each being 0.2 mm apart from the other. The characters 26 indicate attributes of the knife. In this example, the characters 26 include marks "SLIT" which indicates that a type of knife is a slit knife and numeral "3.2" which indicates that a width of the cutting edge (blade) is 3.2 mm.

Since this knife shows a type and size thereof, a surgeon can recognize the knife he/she is using through the monitor of the microscope. If the knife is improper, the surgeon can immediately discover this fact. Therefore, it is possible to avoid using an improper knife in the surgical operation.

The scale 25 provided at the tip of the surgical knife 20 makes the surgeon possible to insert the knife more accurately in the incision. In a cornea surgical operation, for example, very precise and complicated cutting is required, such as "a depth of knife insertion in the first incision is ½ thickness of cornea". In the conventional technology, the surgeon makes such incisions based on his/her intuition, which requires a long experience. In the surgical knife of the present invention, because it includes the scale 25, an accurate depth of cut is known to the surgeon, which makes the surgical operation easy and reliable.

During the process of forming the anti-reflection means, the area of the scale 25 and the characters 26 are masked, thereby easily forming the scale and characters without having anti-reflection treatment.

Although the example of scale 25 includes five lines, different number of lines such as a single line, or six or more lines are also possible. Further, numerals may also be incorporated to show an absolute distance from the tip of the knife. Instead of the lines in the scale 25, it is also possible to use other marks such as dots, patterns, shapes and the like.

FIGS. 3(a)-3(g) are schematic diagrams showing an example of process for producing a surgical knife of the present invention.

First, the rod material 15 is cut in predetermined length as shown in FIG. 3(a). The rod material 15 can have various shapes such as a pole shape, a rectangular shape, a plate shape, etc. Then, in FIG. 3(b), one end of the rod 15 is flattened, and the unwanted tip portion shown by the dotted line is cut out. The flattened surface 15' is cut in a desired shape and is further flattened to have a predetermined thickness t as shown in FIGS. 3(c) and 3(d) through a grinding and/or polishing process. An anti-reflection treatment is performed on the surface 15' through, for example, a sandblast process in FIG. 3(e). Then, in FIG. 3(f), a rough machined surface 13 is produced through a rough cutting process. Finally, a cutting edge 11 is formed at an outer edge of the surface 15' through a polishing process. Depending on the material of the knife, a quenching process may be further conducted.

As the material of the rod, stainless steel such as SUS302, SUS304, SUS420 are mainly used. In the case where the rod has a flat shape, such material as titanium, diamond, ruby, sapphire and ceramic can also be used.

Several methods can be used to form the scale and characters on the surface of the knife. In one method, the scale and characters are masked before the process of the anti-reflection treatment so that the scale and characters do not have the anti-reflection treatment. In the other method, after conducting the anti-reflection treatment on the surface of the knife, the scale and the characters are formed through a grinding process or a pressing process.

As has been described, according to the present invention, since the surgical knife has the anti-reflection treatment on the overall area except for the cutting edge, it can maintain the sharpness of the cutting edge while preventing the glare from the knife during the surgical operation. Thus, the surgeon can perform the operation accurately without being affected by the glare.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A method of producing a surgical knife, comprising the following steps of:

flattening an end portion of a rod material and cutting off an unwanted portion of the rod material;

forming a central flat surface of the surgical knife of predetermined thickness by grinding the flattened end portion;

applying an anti-reflection treatment using a sandblasting process to the central flat surface;

forming a rough machined surface on an outer area of the central flat surface; and forming a cutting edge at an outer area of the rough machined surface;

wherein said rough machined surface formed at along an inside of the cutting edge and said central flat surface adjacent to said rough machined surface have angles different from one another.

2. A method of producing a surgical knife as defined in claim 1, wherein a width of the cutting edge measured horizontally is about 0.15 mm, and a width of the rough machined surface measured horizontally is about 0.35 mm.

* * * * *